United States Patent
Powell

(10) Patent No.: US 6,757,061 B2
(45) Date of Patent: Jun. 29, 2004

(54) METHOD AND DEVICE UTILIZING REAL-TIME GAS SAMPLING

(75) Inventor: Gary Powell, Petaluma, CA (US)

(73) Assignee: Lightwind Corporation, San Francisco, CA (US)

(*) Notice: Subject to any disclaimer, the term of this patent is extended or adjusted under 35 U.S.C. 154(b) by 0 days.

(21) Appl. No.: 10/321,130

(22) Filed: Dec. 17, 2002

(65) Prior Publication Data

US 2003/0133106 A1 Jul. 17, 2003

Related U.S. Application Data

(63) Continuation of application No. 09/726,195, filed on Nov. 29, 2000, now Pat. No. 6,538,734.

(51) Int. Cl.[7] .................................................. G01J 3/30
(52) U.S. Cl. ........................................ 356/316; 356/219
(58) Field of Search ............................. 356/316, 219, 356/246, 454, 417, 72, 451, 244; 422/58.1, 22.05

(56) References Cited

U.S. PATENT DOCUMENTS

| | | | |
|---|---|---|---|
| 3,734,631 A | * | 5/1973 | Justice et al. ............... 356/434 |
| 4,147,431 A | | 4/1979 | Mann |
| 4,148,612 A | * | 4/1979 | Taylor et al. ................. 436/35 |
| 4,270,091 A | | 5/1981 | Mann |
| 4,309,187 A | * | 1/1982 | Dodge et al. ................. 436/35 |
| 4,609,426 A | | 9/1986 | Ogawa et al. |
| 4,615,761 A | | 10/1986 | Tada et al. |
| 4,844,767 A | | 7/1989 | Okudaira et al. |
| 4,847,792 A | | 7/1989 | Barna et al. |
| 4,857,136 A | | 8/1989 | Zajac |
| 4,859,277 A | | 8/1989 | Barna et al. |
| 4,883,560 A | | 11/1989 | Ishihara |
| 5,082,517 A | | 1/1992 | Moslehi |
| 5,160,402 A | | 11/1992 | Cheng |
| 5,273,610 A | | 12/1993 | Thomas, III et al. |
| 5,326,975 A | | 7/1994 | Barna |
| 5,372,783 A | | 12/1994 | Lackie |
| 5,431,734 A | | 7/1995 | Chapple-Sokol et al. |
| 5,473,162 A | * | 12/1995 | Busch et al. ............. 250/341.6 |
| 5,546,322 A | | 8/1996 | Gifford et al. |
| 5,671,045 A | | 9/1997 | Woskov et al. |
| 5,777,735 A | | 7/1998 | Reagen |
| 5,841,651 A | | 11/1998 | Fu |
| 5,857,890 A | | 1/1999 | Ferran |
| 5,877,032 A | | 3/1999 | Guinn et al. |
| 5,949,193 A | | 9/1999 | Roine et al. |
| 5,963,336 A | | 10/1999 | McAndrew et al. |
| 5,986,747 A | | 11/1999 | Moran |

(List continued on next page.)

FOREIGN PATENT DOCUMENTS

JP   58084431 A   5/1983

OTHER PUBLICATIONS

Danner et al., "Downstream Atomic Monitoring for Absolute Etch Rae Determinations", J. Electrochem. Soc: Solid–State Science and Technology (Apr. 1983).

Lichtman, "Residual Gas Analysis: Past, Present and Future", J. Vac. Sci. Technol. A8(3) May/Jun. 1990, 1990 American Vacuum Society.

*Primary Examiner*—Thien M. Le
(74) *Attorney, Agent, or Firm*—Ernest J. Beffel, Jr.; Haynes Beffel & Wolfeld LLP

(57) ABSTRACT

Aspects of the present invention provide novel methods and devices for sampling gas, exciting the sampled gas to emit radiation and detecting in real time from the emitted radiation a plurality of wave bands of an emission spectrum. Energy used to excite the sampled gas may be adjusted based on the detected wave bands. A process may be controlled in real time based on the detected wave bands. Novel interfaces may be used to display portions of the detected wave bands. A known flow of a reference gas may be included in the flow of sampled gases and an unknown flow of an unknown flow gas determined.

72 Claims, 10 Drawing Sheets

U.S. PATENT DOCUMENTS

| | | |
|---|---|---|
| 6,045,618 A | 4/2000 | Raoux et al. |
| 6,046,796 A | 4/2000 | Markle et al. |
| 6,068,783 A | 5/2000 | Szetsen |
| 6,075,609 A | 6/2000 | Tarkanic et al. |
| 6,120,734 A | 9/2000 | Lackie |
| 6,134,005 A | 10/2000 | Smith, Jr. et al. |
| 6,366,346 B1 | 4/2002 | Nowak et al. |
| 6,381,022 B1 | 4/2002 | Zavracky |
| 2002/0093652 A1 | 7/2002 | Powell |

\* cited by examiner

METHOD AND DEVICE UTILIZING REAL-TIME GAS SAMPLING

RELATED APPLICATIONS

This application is a continuation of application Ser. No. 09/726,195 filed Nov. 29, 2000 now U.S. Pat. No. 6,538,734.

BACKGROUND OF THE INVENTION

1. Field of the Invention

The present invention relates real-time gas sampling and spectral analysis.

2. Description of Related Art

Semiconductor manufacturing has adopted various telemetry techniques utilizing mass spectrometry or spectrographical analysis to improve the cleaning, conditioning or operation of reaction chambers in which a variety of reactions take place, such as deposition, cleaning, etching, implantation, ashing, etc. Telemetry techniques help operators monitor processes which take place on a microscopic level inside a closed chamber which often is sensitive to any form of outside radiation.

SUMMARY OF INVENTION

One aspect of the present invention includes sampling gas outside a reaction chamber that has passed through the reaction chamber during a process, wherein the gas diffuses into an excitation chamber. In the excitation chamber, exciting the sampled gas, using at least one external electrode, to emit radiation. And, detecting in real time from the emitted radiation a plurality of wave bands of an emission spectrum. Energy used to excite the sampled gas may be adjusted based on the detected wave bands. A process may be controlled in real time based on the detected wave bands. Novel interfaces may be used to display portions of the detected wave bands. A known flow of a reference gas may be included in the flow of sampled gases and an unknown flow of an unknown flow gas determined. Other aspects of the present invention are set forth in the claims.

DETAILED DESCRIPTION

The following description of various aspects and embodiments of the invention is presented for purposes of illustration and description. The description is not intended to limit the invention to the precise forms disclosed Many modifications and equivalent arrangements will be apparent to people skilled in the art.

Figure 1:
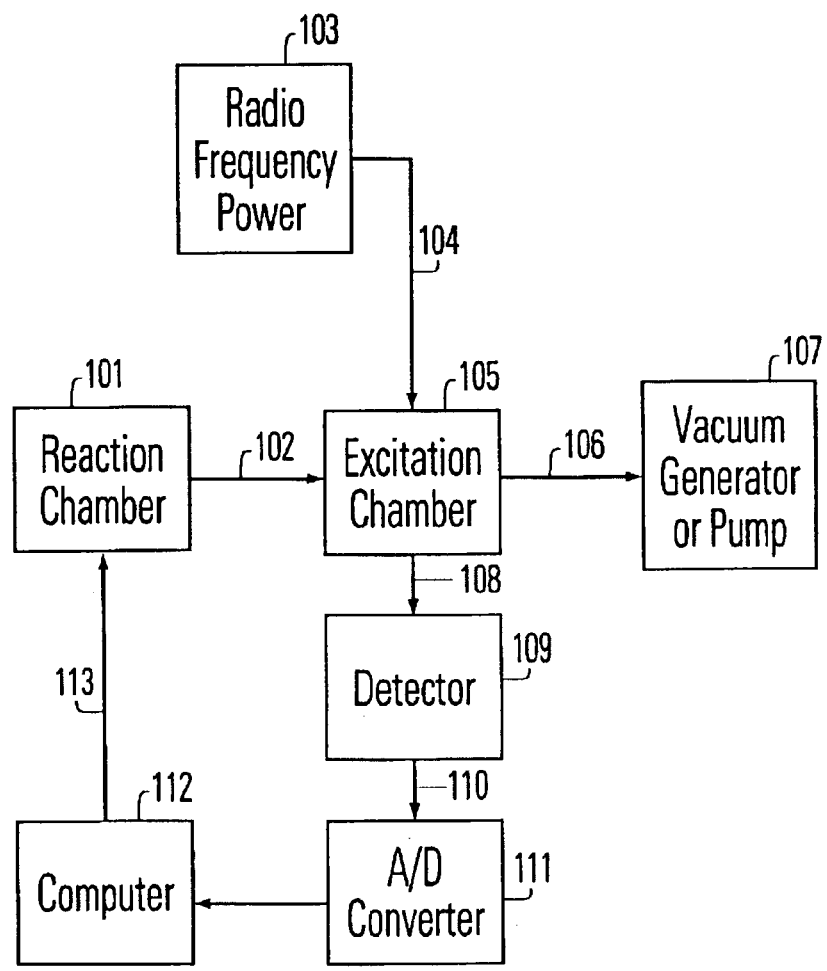
FIG. 1 is a schematic diagram of a system practicing aspects of the invention.

FIG. 1 shows a schematic overview of a system including a useful plasma source and a detector. Gas samples from a reaction chamber 101 are communicated 102 to an excitation chamber 105. The process in the reaction chamber broadly may include a calibration of gas flow through mass flow controllers, checking for a leak or any of a variety of reactions, such as deposition, cleaning,. etching, implantation, ashing, etc. The communication of sampled gas may correspond to one or more exhaust streams from the reaction chamber or any other outlet from the reaction chamber. The sampled gas may be representative of material supplied to the reaction chamber, plasma created in the reaction chamber, or exhaust gas containing byproducts of a reaction taking place in the reaction chamber; alternatively, the gas need not be representative, but should have a reproducible relationship to some factor of interest.

The excitation chamber 105 is connected by a cable 104 to a radio frequency power source 103. The excitation chamber 105 may be capacitively or inductively coupled to the sampled gas. Alternatively, a system could practice aspects of the present invention utilizing microwave or cyclotron radiation, or utilizing internal electrodes such as arc electrodes to excite the sampled gas to a plasma state in which it emits radiation. In FIG. 1, the sampled gas is drawn through or past the excitation chamber 105 by communication 106 with a vacuum generator or pump 107. The sampled gas may reach the excitation chamber 105 by direct flow through the chamber or by diffusion into the chamber.

The sampled gas in the excitation chamber 105 is excited to emit radiation. The emitted radiation comprises an emission spectrum of the sampled gas. The emitted radiation passes through a window or fiber optic cable 108 to a plurality of detectors 109 which are responsive in real time to wave bands of the emitted spectrum. A SMA 905 to single strand optical fiber connector (0.22 NA) may be used. The individual detectors may be photomultiplier tubes, photodiodes, CCD's or other photosensitive components. The individual detectors may be characterized as shallow junction or deep junction devices. A useful characteristic of detectors is quick response time, permitting a scan and A/D conversion of signals from a plurality of detectors in 20 milliseconds or less, which can presently be attained by using shallow junction devices such as shallow junction CCD's. The respective detectors will be sensitive to a plurality of wave bands of the emitted radiation. This may be accomplished by positioning the respective detectors to receive diffracted light from a diffraction grating, by using filters, or by equivalent means. A plurality of detectors receive energy received in their respective wave bands at substantially the same time, though the sensitivity of individual detectors to particular wave bands may be increased by varying the integration time among the respective detectors.

A useful configuration of detectors and a diffraction grating includes spacing the detectors in relation to the diffracted light so the detectors are responsive to band widths sufficiently narrow that a plurality of detectors are responsive to a single peak in an emission spectrum. A prepackaged device capable of focusing detectors on wave bands of 1.23 nm FWHM bandwidth is a Sony ILX511 device. It includes a 2,048 detector CCD array and a diffraction grating. Individual elements are 12.5 mm×200 mm. The well depth of an individual element at 600 nm is 160,000 photons. The estimated sensitivity may be expressed as 86 photons/count, $2.9 \times 10^{-17}$ joule/count, or $2.9 \times 10^{-17}$ watts/count for 1-second integration. Its effective range is 200–1000 nm and its integration time may be 3 ms with a 1 MHz A/D card or 4 ms with a 500 kHz A/D card. The Sony IXL511 device can be configured with a grating which diffracts radiation in the 200 to 850 nm spectrum. A slit of 25 mm is typical, with 10, 50 and 100 mm slits available. Various combinations of groove density, fiber diameter and slit width can be selected for additional sensitivity or a wider spectral range. Optics suitable to UV radiation in the 200–350 nm range are used. Order sorting is accomplished with a single-piece, multi-bandpass detector coating for applications in the 200–850 nm spectrum. Detector enhancements which increase UV sensitivity are susceptible to false signals at shorter wavelengths. A coating is used to reduce the effects of wavelengths that are second or third harmonics of the signal of interest. A scan time for collecting and converting data from the array elements is 20 milliseconds or less. In a cost sensitive application, a more modest array having 1024 or 512 detectors can be used. In an even more cost sensitive application, a plurality of detectors can be used, either with a diffraction grating or with filters which effectively tune the respective detectors to specific wave bands or wave lengths.

Elements of the detector 109 typically are wired 110 to an analog to digital (A/D) converter 111. The output of the A/D converter 111 is connected to a computer 111. When the A/D converter is an A/D card and the computer is a PC or workstation, the connection may be by PCI bus or other bus. A 300 MHz or faster PC with 64 megabytes RAM, a CD-ROM drive, memory for storing programs which operate and control the sampling, exciting and detecting apparatus, and a modem may be equipped with Windows 98 Second Release and Labview 6.1 software. Later versions or alternatives to these OS and data collection software can be used. Custom software provides user and device interfaces. The computer 112 can communicate 113 with controllers for the reaction chamber 101. The computer can control process parameters for the reaction chamber directly, as depicted, through another computer or controller, or by providing data to an operator who controls the process parameters. The computer also can store data collected during operation of the process for later analysis. A further use of the computer, understandable by reference to FIG. 1, is to control the energy used to excite the sampled gas to emit radiation. In some instances, the energy used can be reduced to avoid or reduce saturation of detectors responsive to particular wave bands. In other instances, the energy used can be increased to increase the radiation emitted in particular wave bands.

Figure 2:
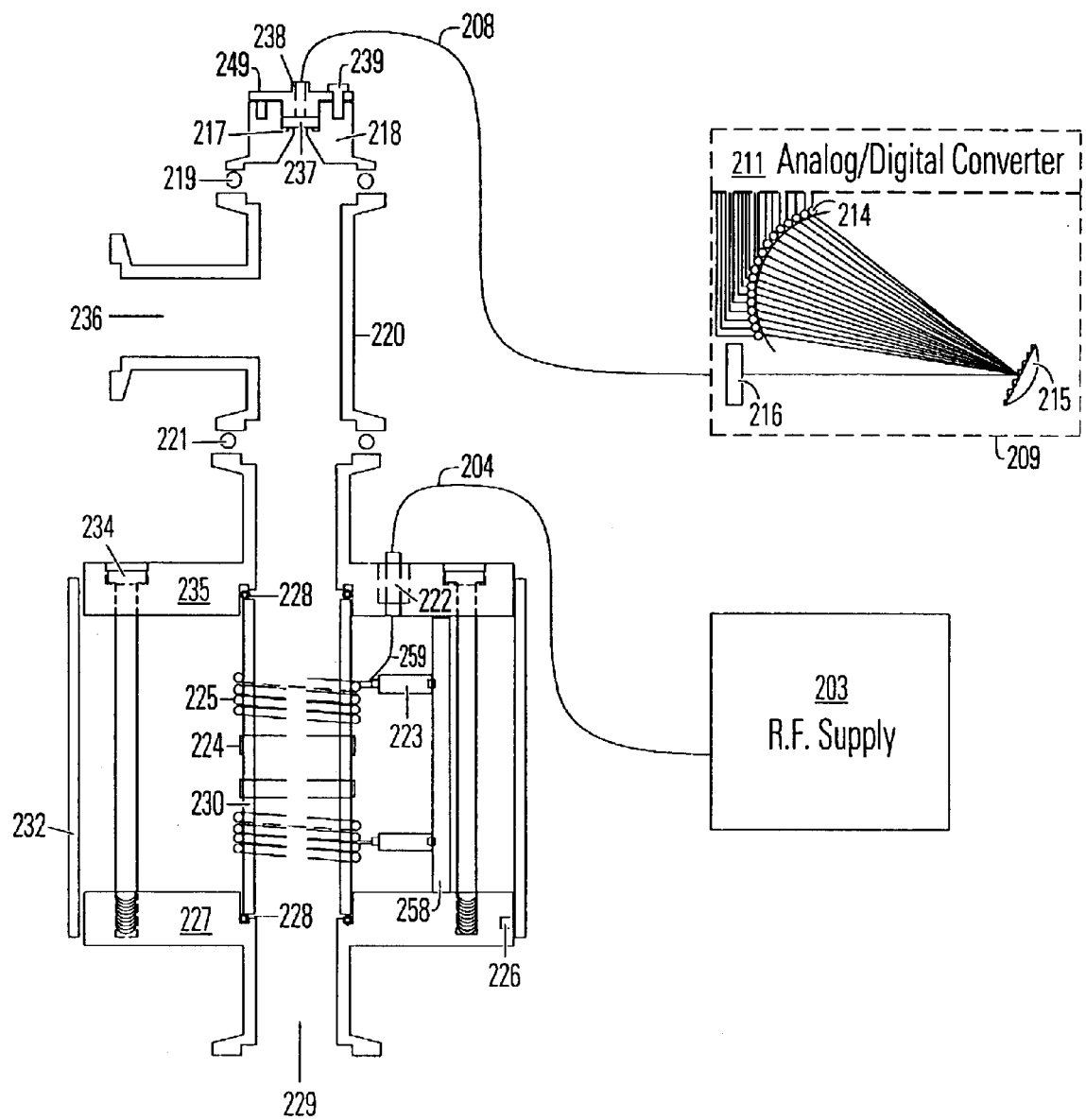
FIG. 2 depicts one configuration of a useful plasma source and detector.

FIG. 2 depicts one configuration of a useful plasma source and detector. This plasma source is inductively and capacitively coupled to the sampled gas in the excitation chamber. With various kinds of shielding, the mode of coupling can be limited. FIG. 2 is a cross-section view. A vacuum "T" 220 connects the reaction chamber (not shown) to an apparatus which excites sampled gas and detects the emitted radiation. The vacuum "T" 220 is connected to the reaction chamber at 236. This connection can be to an exhaust from the reaction chamber or a manifold connecting a plurality of exhausts. Alternatively, this connection can be to at least one sampling port or at least one feed line. At one end, the source input cap 235 is attached to the vacuum "T" 220. A compressible o-ring 221 isolates the sampled gas from ambient gas surrounding the apparatus. The sampled gas typically is at a low pressure, measured in torrs or millitorrs. Effective isolation is provided from ambient gas surrounding the apparatus, which may be atmospheric gas or a clean room gas. The vacuum "T" 220 also is connected to an optical vacuum blank 218, with an additional compressible o-ring 219. A pressure differential between inlet 236 and outlet 229 produces a flow of sampled gas through the excitation chamber 230. When the inlet is connected to at least one exhaust from the reaction chamber, at least a portion of the exhaust gas from the reaction chamber flows through the excitation chamber.

The apparatus which excites gas includes the inlet cap 235, an excitation chamber 230 and an outlet cap 227. O-rings 228 are positioned between the excitation chamber and the caps. Bolts 234 compress the o-rings and secure the caps. A covering 232 surrounds the body of this apparatus. An R.F. power supply 203 is connected by a cable 204 through a bulkhead connector 222 to a connector wire 259. A support 258 positions capacitors 223 which are connected to the connector wire 259, the coil 225 and the external igniter rings 224. In an alternative configuration, an internal igniter exposed to sampled gas in the excitation chamber 230 could be used. In one embodiment, the R.F. power supply 203 broadcasts at 13.56 MHz. This R.F. energy passes through the capacitor 223 into the coil 225 and ignition rings 224. An electrical discharge in the excitation chamber results, causing the sampled gas to emit radiation. To improve power transfer efficiency, a matching network may be added to the source. The impedance of the gases before ignition or initiation of the plasma state is different than after ignition. The igniter bands 224 can be used to capacitively ignite the plasma. The capacitors 223 are charged to a sufficient voltage to break down the gas in the excitation chamber 230. When ignition occurs, the impedance changes and power transfer occurs through the inductive coils 225. A capacitor can be used to adjust the reactance of the circuit. Power can be shunted through a resistor to ground. The combination of passive capacitive and resistive components broadens the effective impedance range through which power can effectively be coupled into the sampled gas. When the sampled gas transitions to a plasma state, its volume changes as a function of the R.F. power input. As the power increases, the gas breakdown and ion generation increase; radiation is emitted. The applied R.F. power for exciting the sampled gas to emit radiation is independent of any plasma source for the reaction chamber.

At the optical vacuum blank 218, a group of screws 239 compress an optical adapter 249 against a window 237 and o-rings 217. The window 237 can be made of sapphire which transmits light from approximately 200 nm into the near infrared region, such as 850 or 1000 nm. The optical adapter 249 mechanically supports a fiber optic connector 238 which provides a quick connection to fiber optic cable 208. The fiber optic cable 208 transmits radiation emitted by the sampled gas to detector 209. Light emerging from the cable 208 enters the detector 209 through a lens 216 which focuses it on a diffraction grating 215. The grating 215 separates the light into a spectrum which is diffracted in an orderly fashion across a detector array 214. The detector array 214 converts photons into electrical energy, generating analog signals proportional to the intensity of photons in the wavebands on which the respective detectors are focused. In alternative embodiments, individual detectors may be located so that they are responsive to specific diffracted wavebands or individual detectors may be equipped with filters so that no diffraction grating is required. An analog to digital converter 211 is connected to the detectors. It scans the detectors and converts their analog outputs to digital signal.

Figure 3:
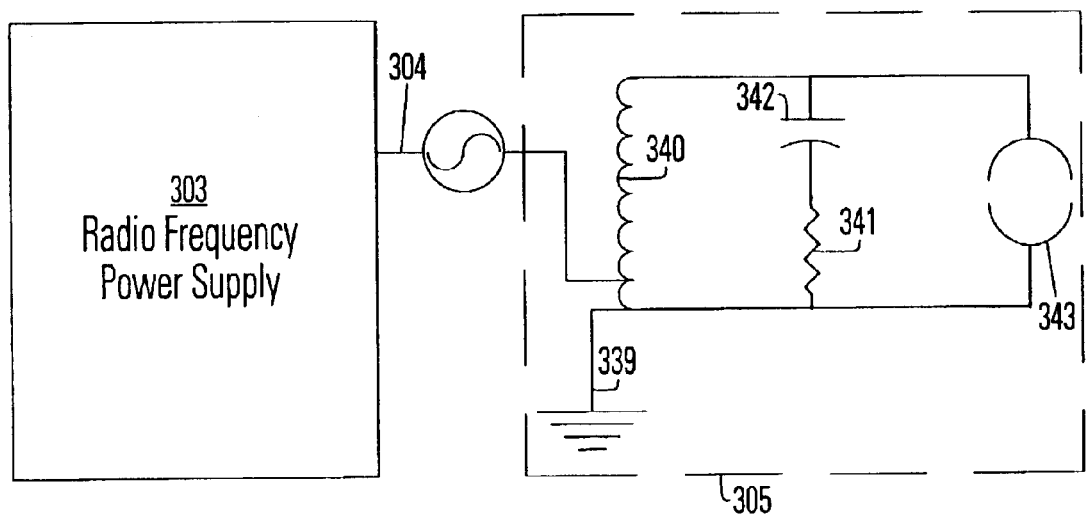
FIG. 3 is a simplified schematic view of a radio frequency power supply and power transfer section.

FIG. 3 is a simplified schematic view of a radio frequency power supply and power transfer section. An R.F. power supply 303 generates an R.F. signal which is coupled 304 to a power transfer section 305. The power transfer section comprises a coil or inductor 340, a resistor 341, a capacitor 342, ignition rings 343 and a ground 339. The ignition rings function as a capacitor under certain conditions.

Figure 4:
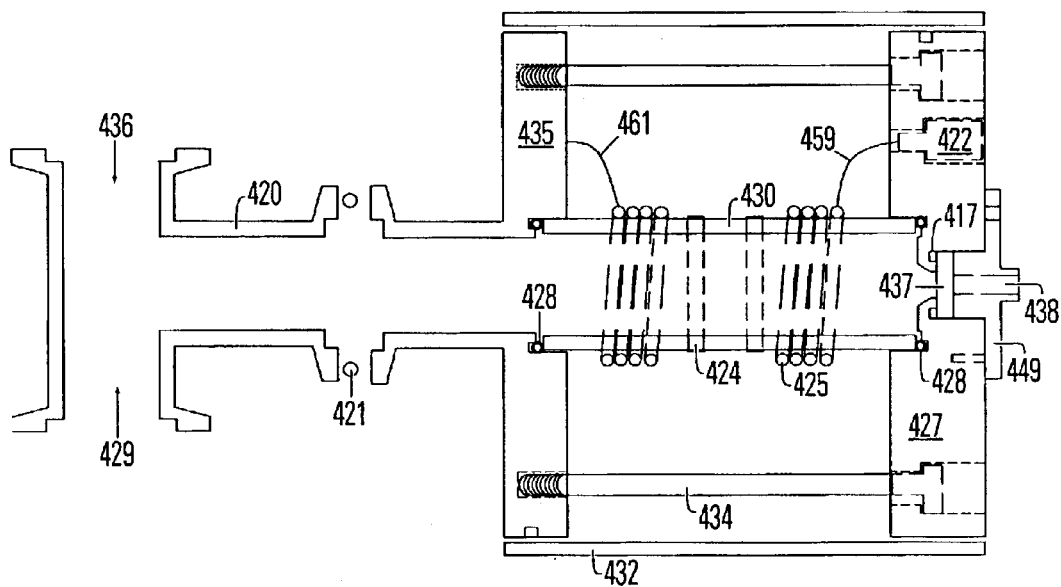
FIG. 4 is an alternate configuration of a useful plasma source and optical fiber connector.

FIG. 4 is an alternate configuration of a useful plasma source and optical fiber connector. In this configuration, the vacuum "T" allows sampled gas to diffuse through the excitation chamber, rather than flowing through it. The numbering of elements in FIG. 4 generally corresponds to the numbering of elements in FIG. 2. A pressure differential causes gas to flow from the inlet 436 to outlet 429. Gas diffuses through the connector 420 and inlet cap 435 into excitation chamber 430. Isolation from ambient gas is maintained and various junctures by o-rings 421, 428 and 417. The inlet cap 435 is compressed against the excitation chamber 430 and the optical adapter cap 427 by bolts 434. An R.F. bulkhead adapter 422 receives an R.F. signal and communicates the signal along connector wire 459 to a coil 425. In this figure, charging capacitors for the igniter rings 424 are not depicted. A ground wire 461 connects to the coil or inductor 425. The optical vacuum blank 449 is secured against a window 437. It includes an optical fiber connector 438. A covering 432 surrounds this portion of the apparatus. The configuration in FIG. 4 is adapted to a different gas flow than the configuration in FIG. 2. For production purposes, the similar components may be used in the two configurations.

Figure 5:
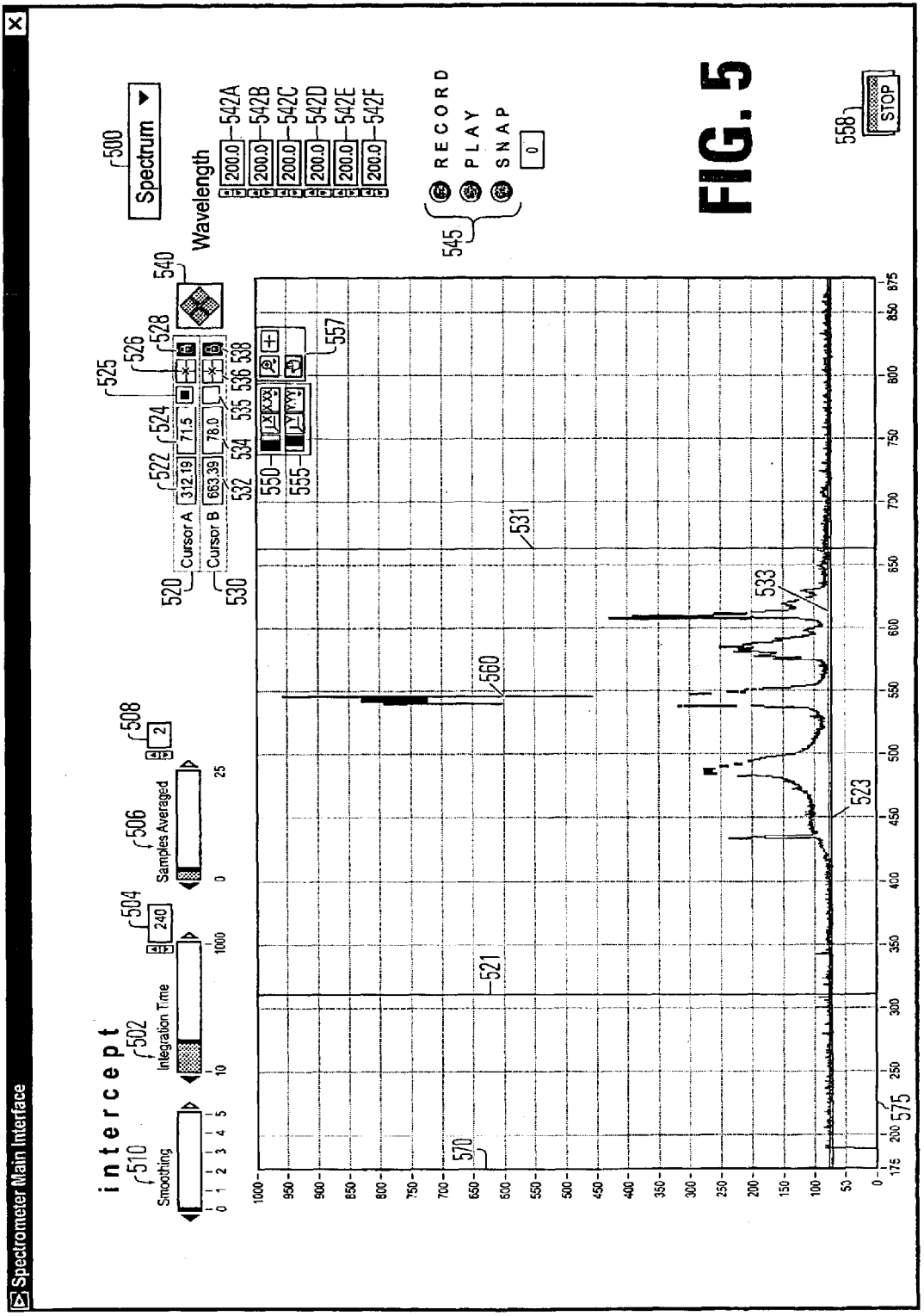
FIGS. 5–8 are interfaces between the user and a system utilizing aspects of the present invention.

FIG. 5 depicts a graphical interface which practices aspects of the present invention. This is the "spectrum" interface, selected using a pull down list 500. Certain interface controls are common to this and other interfaces. Integration time for producing integrated detections may alternately be controlled by dragging a slide bar 502 or entering a value 504. The integration time controls the accumulation and reset of charges in the individual detectors. In this figure, a single integration time is depicted. Alternatively, the integration time could vary across wavebands of a spectrum of emitted radiation, to compensate for variable sensitivity of detectors across wavebands or to produce a greater signal gain in portions of the spectrum where faint peaks are expected. The interface control for integration time would then be a scaling factor, rather than a number of milliseconds. The number of integrated detections to be averaged together may alternately be controlled by dragging a slide bar 506 or entering a value 508. The samples averaged are the number of samples which are averaged produce a point of data for display. In this interface embodiment, sampling of 1 to 25 integrated detections is depicted. Smoothing is controlled by a slide bar 510. Many types of smoothing can be applied, such as boxcar and moving average smoothing. This interface embodiment depicts smoothing factors in the range of 0 to 5. Cursor controls 520 and 530 also are common among interfaces. Two separate cursors are provided in this embodiment. Placement of the cursor is controlled by the user when the cursor tool 526, 536 is active and the cursor lock 528, 538 is inactive. Controls 525 and 535 turn on either or both cursors or crosshairs displayed on the screen. Those crosshairs are moved by selecting and dragging, or by incremental stepping with control 540. As a user drags the cursor to a location, numeric readouts are displayed for wavelength 522, 532 along the x-axis 575 and a measure of intensity 524, 534 along the y-axis 570. The crosshairs corresponding to cursor A appear as lines 521 and 523; the crosshairs for cursor B are lines 531 and 533. Control 540 steps the selected crosshairs left, right up or down in increments of one pixel. Wavelength selection 542A–E also is common to several interfaces, but is not active for the "spectrum" interface, because no single wavelength is tracked or graphed. In other interfaces, the user may select up to six different wavelengths to track. The stop button 558 is shared among interfaces. Controls 550, 555 and 557 also are common. Controls for the x-axis 550 and y-axis 555 set the range covered by the respective axises and the format of the axis labels. Mouse cursor controls 557 control zooming, centering and repositioning the display. Particular to the "spectrum" interface are button controls 545 and the line graph 560 depiction of the detected spectrum of emitted radiation from the excited sampled gas.

Figure 6:
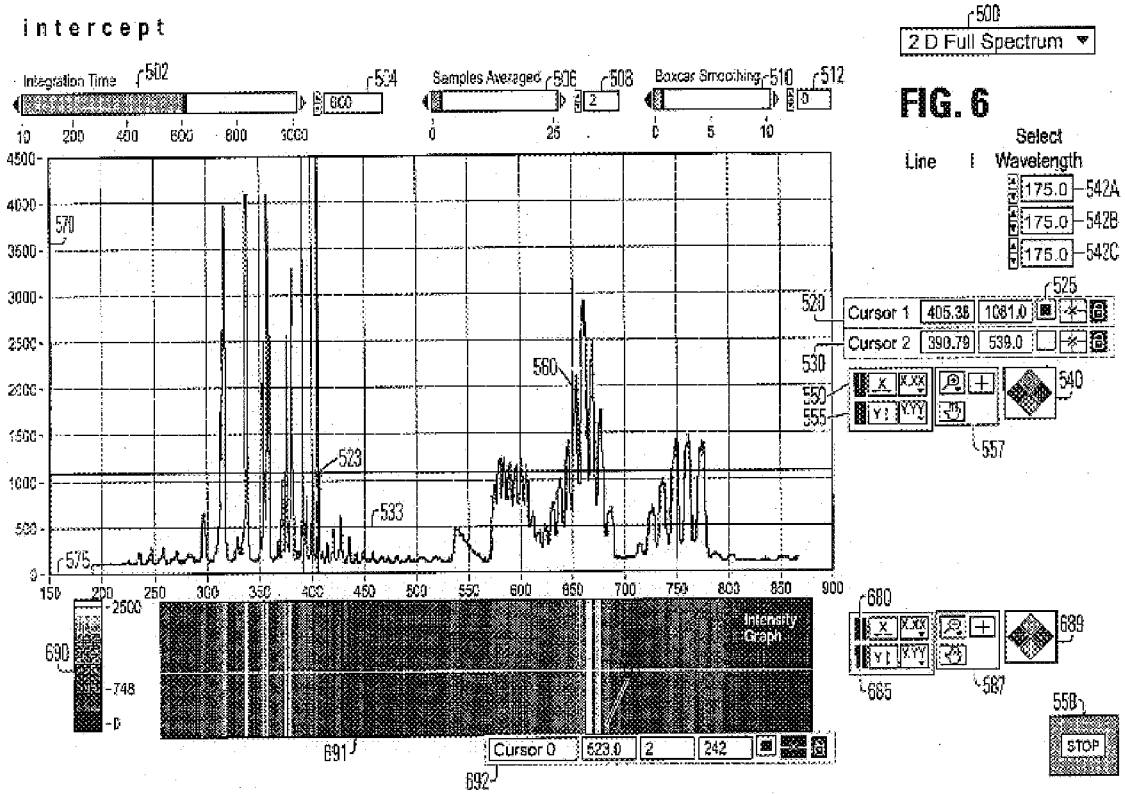

FIG. 6 depicts the "2 D full spectrum" interface. This interface includes the line graph and numerical readouts of the "spectrum" interface, plus an intensity graph. The numbering of interface elements in FIG. 6 is repeated from FIG. 5, to the extent applicable. Differences include fewer (still inactive) wavelength selection options 542A–C and a numerical smoothing selection control 512, in addition to the slider smoothing selection control 510. The intensity graph 691 appears in this embodiment as a bright line spectrum, wherein peaks of spectral intensity are represented by light colors. In a full color display, a range of dark blue to white or any other color range could be substituted for black to white. An alternative display could be in a dark line format. The bright line format is preferred, because it is more commonly used for emission spectrums, whereas the dark line format is used for absorption spectrums. An intensity scale 690 is provided. This intensity scale may top out or saturate at a different value than the top intensity value for the line graph. Controls for the x-axis 680 and the y-axis 685 correspond to controls 550 and 555. Mouse cursor controls 687 and 689 correspond to 557 and 540. The Cursor 0 controls 692 generally correspond cursor 1, 2 controls 520, 530. Controls 687 include a hand which moves the graph around. The magnifying glass invokes a pop-up menu that allows zooming in or out on selected portions of the graph. Control 689 has the same effect as control 540. The line graph and intensity graph provide a pair of readouts for spectral data, complemented by the additional numerical readouts associated with the cursors.

Figure 7:
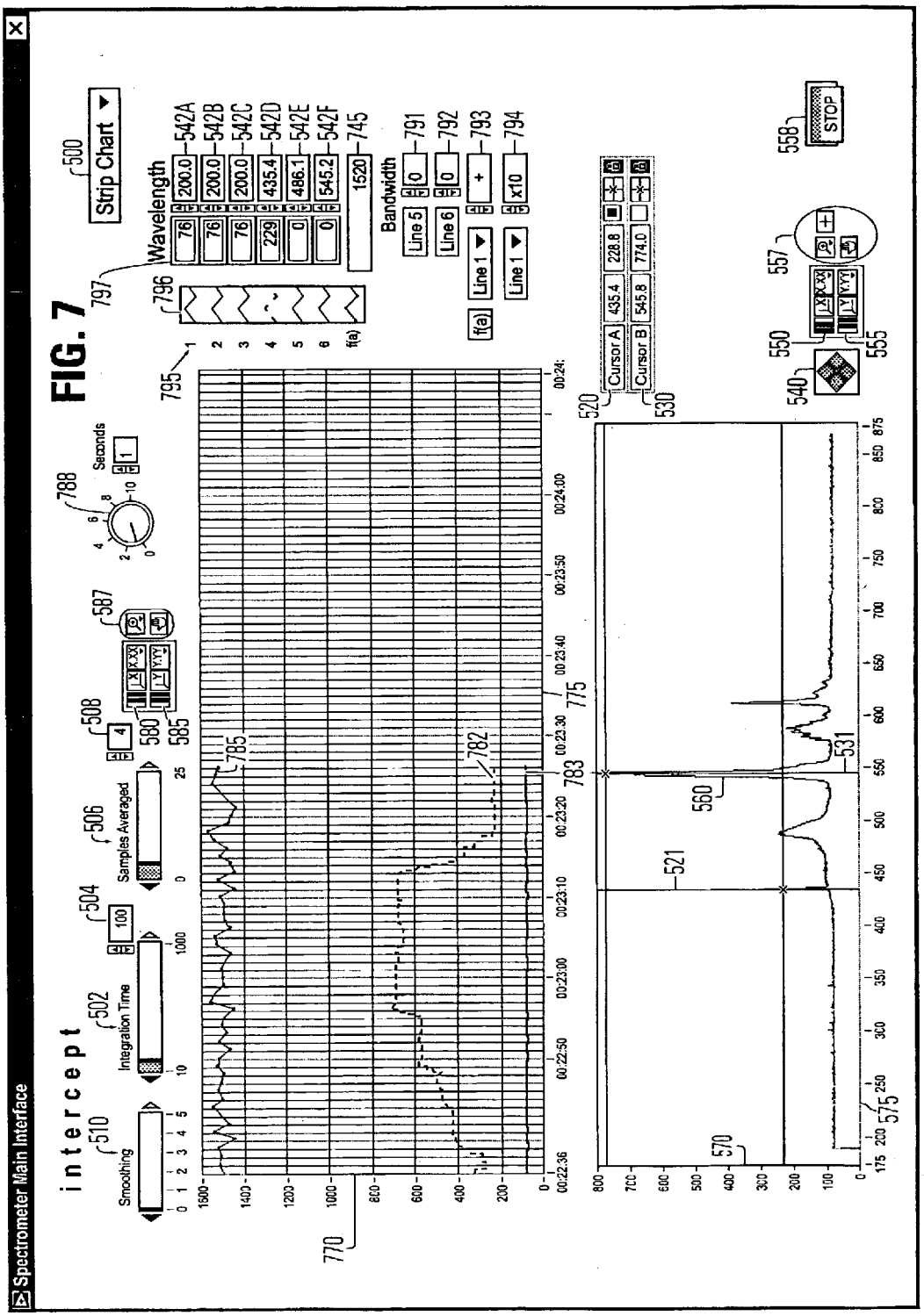

FIG. 7 depicts a "strip chart" interface which combines readout features of the "spectrum" interface in FIG. 5 with a strip chart and algebraic function readout. The numbering for the spectrum display in the lower half of FIG. 7 corresponds to the numbering of FIG. 5. A number of elements are added for the strip chart display in the upper half of FIG. 7. A seconds control 788, including an indicator knob and a numeric entry window control the x-axis (775) of the strip chart. The wavelength selector controls 542A-F are operative for the strip chart. Complementary to these controls are a spectral line number 795, a color legend 796, and a current intensity value for each of the spectral lines. Controls 542 select the wavelengths that will be tracked on the strip chart recorder graph 720. The numeric intensity readout for each line is the 797 column. Note that the intensity values of 0 correspond to a bandwidth of 0 for spectral lines 5, 6. The intensity values of 76 correspond to background levels for spectral lines 1–3. The spectral line number f(a) and related controls 745 are for a function of other selected spectral lines or wavebands. Bandwidths for selected spectral lines are directly controllable 791, 792. A displayable function f(a) of two selected spectral lines or wavebands can be constructed using controls 793 and 794. This embodiment depicts an algebraic combination of the form x+ay, where a=10. Alternatively, any other algebraic function could be displayed. For instance, a derivative function, tracking the slope of a spectral line over time or the curvature of a spectral line could be tracked. In FIG. 7, strip chart line 782 corresponds to spectral line 4 (542D). Line 783 corresponds to spectral line 1 (542A) and line 785 corresponds to f(a) (793+794), which, as depicted, is 11 times the magnitude of spectral line 1 (542A).

Figure 8:
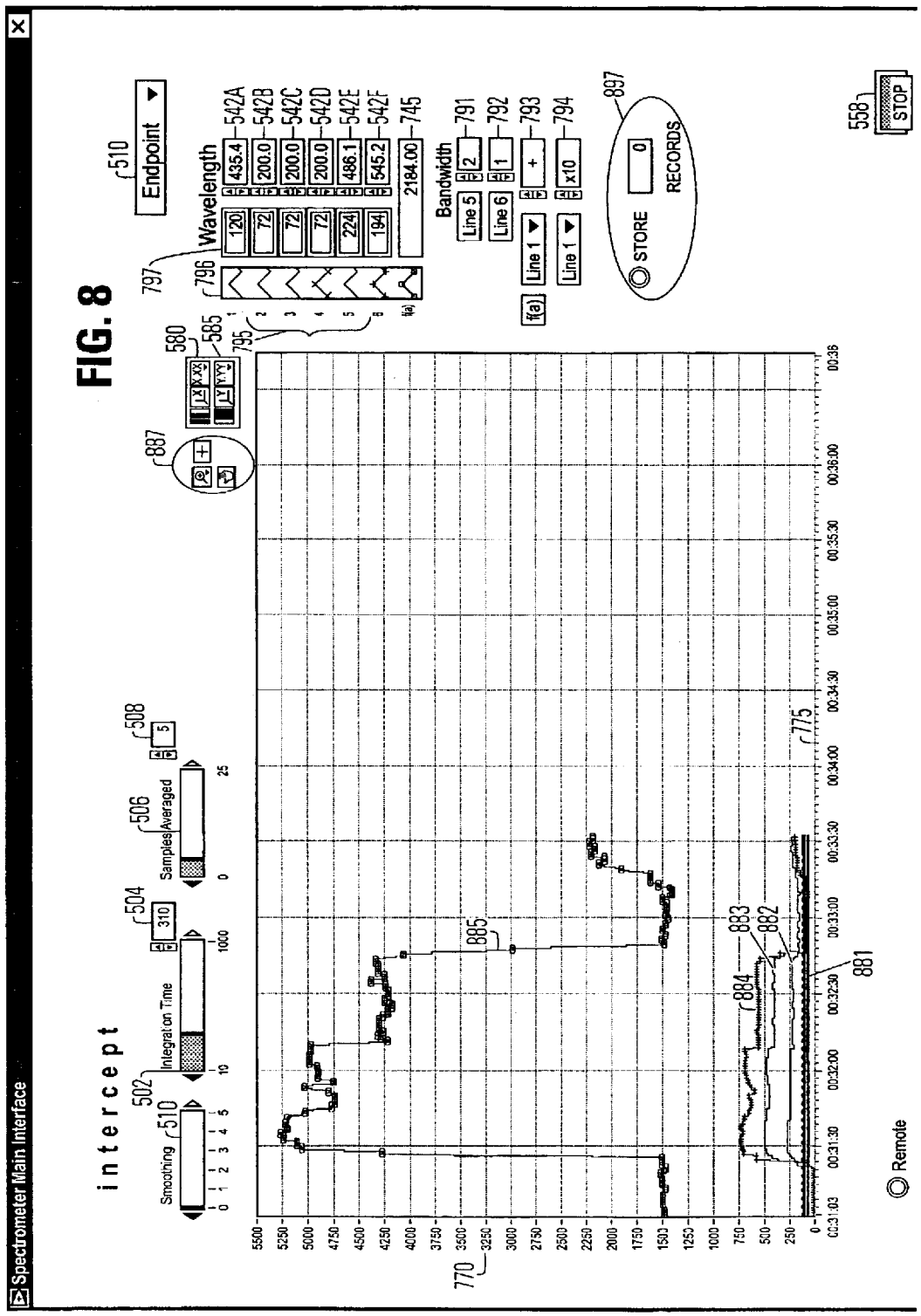

FIG. 8 depicts an "endpoint" interface which includes the readout features of the top half of the "strip chart" interface of FIG. 7. In this figure, line 881 corresponds to the background levels of spectral lines 2–4. Line 882 corresponds to spectral line 1. Line 883 corresponds to spectral line 5. Line 884 corresponds to spectral line 6. Line 885 corresponds to spectral line f(a) (745). A button is added to this interface to allow a user to trigger storage of a specified number of records 897.

Figure 9:
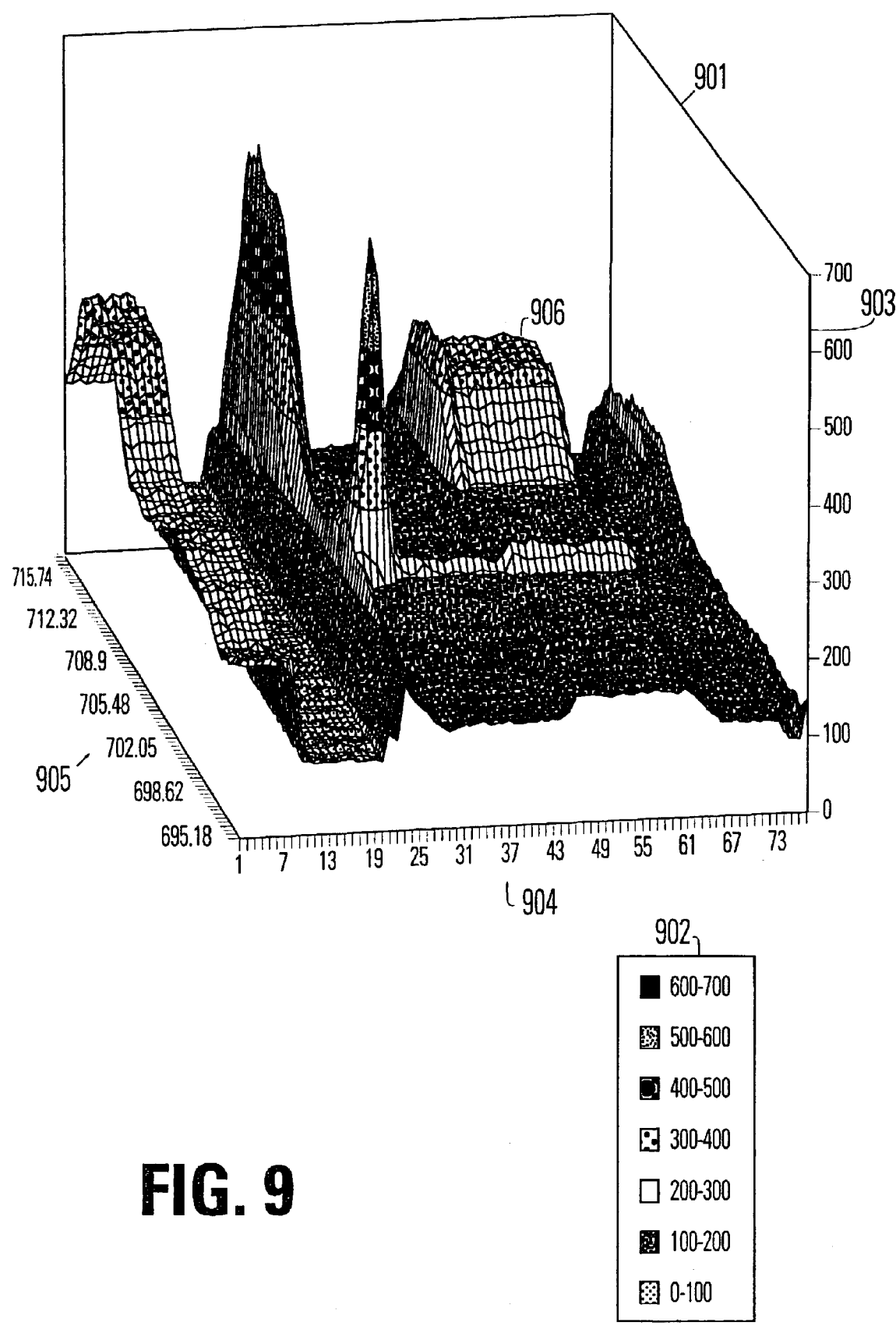
FIG. 9 depicts a 3-D map of gas changes through a full nitride etch cycle.

Records saved from the spectral history of a process can be analyzed as shown in FIG. 9. The three dimensional presentation of this data is framed 901. The legend 902 assigns colors to different levels of intensity. Z-axis scale 903 is a measure of emitted radiation intensity in each of the wave bands. X-axis scale 904 corresponds to time. Y-axis scale 905 corresponds to wavelengths of measured radiation. The shaded wireframe 906 presents the data.

The data in FIG. 9 shows a portion of the emission spectrum, from 695 to 718, nm wavelengths, for a full nitride etch cycle. This 3D presentation assists an operator in understanding changes in reaction byproducts produced during the etch. Key wavelengths to monitor can be identified and characteristic rises and falls in emission intensity can be gauged. Straight forward review of this or a similar data presentation can enable an operator to set parameters for an endpoint process control for this nitride etch cycle or another process.

Figure 10:
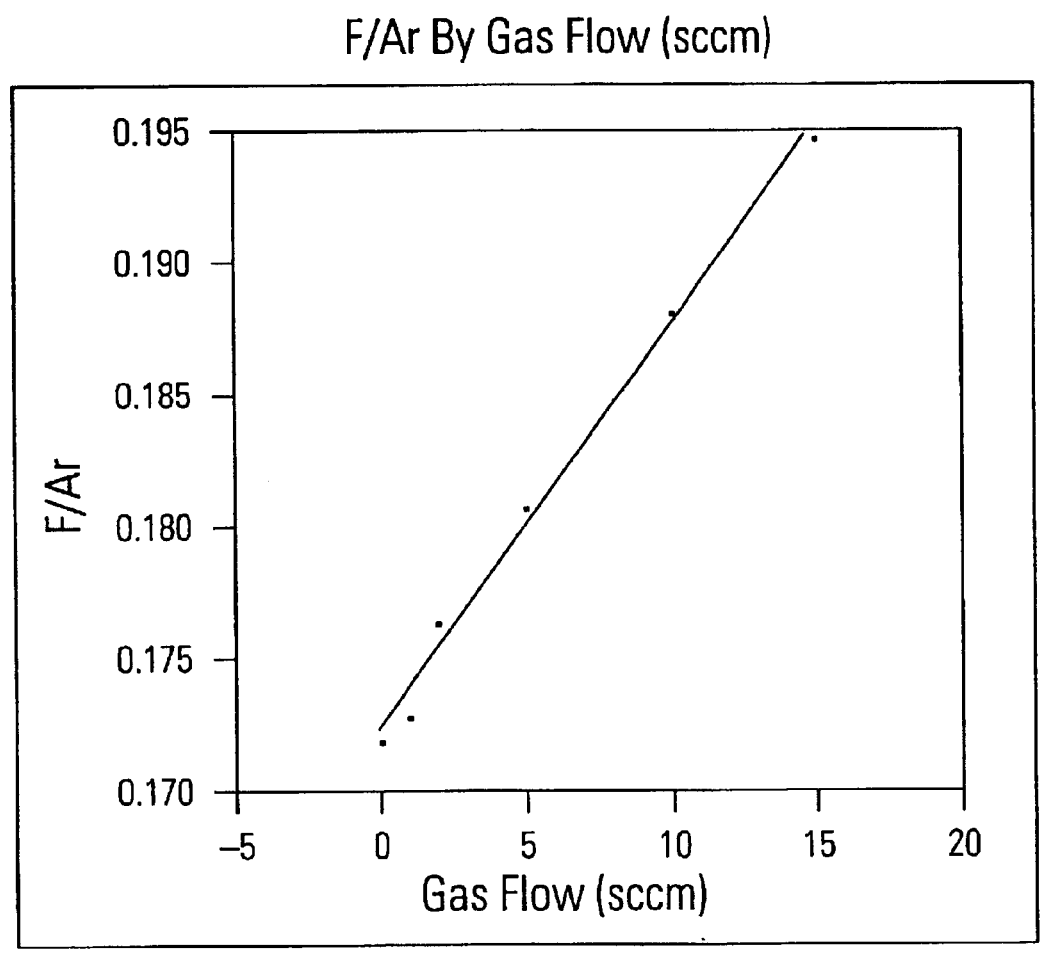
FIG. 10 graphs results of calibration tests for introducing a reference gas to the gases exhausted from a reaction chamber.

FIG. 10 depicts a process in which a reference gas is used to determine quantitatively the amount of fluorine in an exhaust stream. The peaks analyzed were fluorine at 704 nm and argon at 750 nm. The data in this figure are from tests run on a Lam XL etcher, using gas flow but no plasma discharge in the reaction chamber. A gas flow including 500 sccm argon was initiated. Varying quantities of $CF_4$ gas, from 1 to 20 sccm, were introduced. By flow, the fluorine was sometimes less than 0.002 percent of the total flow. With stable flows, peaks for fluorine and argon were measured. A ratio of the measured intensities of the peaks F(704)/Ag (750) was calculated for each quantity of $CF_4$ gas. The ratios were graphed in FIG. 10. Linear regression was used to fit the ratios. The following table summarizes the fit:

| Linear Fit | | | | |
|---|---|---|---|---|
| F/Ar = 0.17249 + 0.00153 Gas Flow (sccm) | | | | |

| Summary of Fit | |
|---|---|
| RSquare | 0.991784 |
| RSquare Adj | 0.98973 |
| Root Mean Square Error | 0.000915 |
| Mean of Response | 0.180879 |
| Observations (or Sum Wgts) | 6 |

| Analysis of Variance | | | | |
|---|---|---|---|---|
| Source | DF | Sum of Squares | Mean Square | F Ratio |
| Model | 1 | 0.00040397 | 0.000404 | 482.8533 |
| Error | 4 | 0.00000335 | 0.000001 | Prob>F |
| C Total | 5 | 0.00040732 | | <.0001 |

| Parameter Estimates | | | | |
|---|---|---|---|---|
| Term | Estimate | Std Error | t Ratio | Prob>\|t\| |
| Intercept | 0.1724864 | 0.000534 | 322.92 | <.0001 |
| Gas Flow (sccm) | 0.0015259 | 0.000069 | 21.97 | <.0001 |

These fit results demonstrate quantifying an unknown flow gas through the reaction chamber, utilizing measurements of intensity of the known spectral peaks of an unknown flow gas and a reference flow gas. In this instance, a linear fit of ratios of the spectral peaks was used. In another instance, a non-linear fit might be more appropriate. Or, a look up table could be indexed using the intensity measurements. The quantified flow of the unknown flow gas can, in turn, be used for process control. For instance, a mass flow controller can be recalibrated. Or, an endpoint can be detected based on a change in flow of the unknown flow gas.

Aspects of the present invention include controlling a variety of processes. In a reaction chamber used for deposition, material builds up on the reaction chamber walls which must be periodically cleaned or removed. One removal technique includes using a plasma of gas containing fluorine to etch the chamber walls clean. This process produces characteristic emission lines associated with fluorine, carbon monoxide and oxygen. Monitoring the intensity and changes in the intensity of peaks associated with these process gases and byproducts enables control of the cleaning process.

Plasma etch reactors experience a build up of polymers and other etch byproducts which must be periodically cleaned or removed. A removal technique for these reaction chambers includes using plasmas containing oxygen or oxygen and fluorine. By monitoring the fluorine, carbon monoxide or other process gases or etch byproducts, it is practical to determine when the chamber is clean. Ending the cleaning process when the chamber is clean can reduce maintenance time or consumption of cleaning materials.

A reaction chamber which has been cleaned typically needs to be preprocessed and conditioned to develop a desirable build up of materials on the reaction chamber walls. This desirable build up restores process operation to a stable condition. Utilizing data from prior operations, desired byproduct levels for particular plasma conditions can be determined. Conditioning of the reaction chamber can be allowed to proceed until the desired byproduct levels are met. Alternatively, conditioning of the reaction chamber can be allowed to proceed until the conditioning reaction reaches a steady state.

The use of reaction chambers sometimes produces environmentally sensitive byproducts. One environmentally sensitive byproduct which can be monitored, as an aspect of the present invention, is chlorinated fluorocarbons. These chlorinated fluorocarbons may include hydrochlorinated fluorocarbons. Either the exhaust of a wafer handling reaction chamber or a scrubber reaction chamber can be monitored for the presence of the environmentally sensitive byproducts. A process can be controlled to modify process conditions or to suspend processing when the level of environmentally sensitive chemicals exceeds an allowable threshold.

Reaction chambers which operate at pressures significantly below atmospheric pressure can be monitored for contamination with ambient gases. Such processes are susceptible to contamination from gases which leak into a vacuum chamber. The gases may contaminate sputtered films, alter etch chemistries, or degrade various processes in other ways. Spectral peaks can be monitored for the presence of nitrogen, oxygen or other gases present in atmospheric or clean room gases. Processes can be monitored and controlled so that detection of a leak suspends processing or a process sequence immediately or at the end of a process step.

The endpoint of a semiconductor process may be signaled by chemical state changes. For instance, when etching proceeds through a layer intended to be removed into a layer which is not supposed to be removed, the undesired etching produces different byproducts than the desired etching. Spectral peaks can be monitored for decreases in desired byproducts and increases in undesired byproducts. Processes can be controlled so that etching stops when removal of a layer is sufficiently complete and before an underlying layer is excessively damaged.

Hardware failures in an etching reaction chamber produce detectable byproducts. For instance, ineffective clamping of a wafer tends to create elevated helium levels. Processes can be controlled so that the clamping of a wafer is adjusted before it is damaged and the process restarted from where it left off.

Generally speaking, chemical balances in a reaction chamber change during a process. By monitoring exhaust gas, estimates of the chemical concentrations in the chamber may be made and used to modify process parameters, such as parameters controlling the production of plasma in the reaction chamber.

By addition of a flow restrictor to the previously described embodiments, the equipment and methods of the present invention can be applied to sampling gases at or near atmospheric pressure. For instance, smokestack and tailpipe gases can be monitored. Compliance with emission control requirements can be monitored continuously. Industrial processes can be modify or suspended when emissions exceed allowable levels. Automobiles can be approved or disapproved for smog control, based on observed levels of emissions. The fuel/air mixture to an engine can be modified during operation, based on observed emission byproducts.

While the present invention is disclosed by reference to the embodiments and examples detailed above, it is understood that these examples are intended in an illustrative rather than in a limiting sense. It is contemplated that modifications and combinations will readily occur to those skilled in the art, which modifications and combinations will be within the spirit of the invention and the scope of the following claims. Each method practicing the present invention may readily be recast as a device or article of manufacture.

What is claimed is:

1. A method of obtaining data regarding a process in a reaction chamber, comprising:
   sampling gas outside a reaction chamber that has passed through the reaction chamber during a process, wherein the gas diffuses into an excitation chamber;
   exciting the sampled gas, using at least one external electrode, to emit radiation; and
   detecting in real time from the emitted radiation a plurality of wave bands of an emission spectrum.

2. The method of claim 1, wherein the sampled gas is from at least one exhaust gas stream.

3. The method of claim 1, wherein the external electrode couples inductively to the sampled gas.

4. The method of claim 1, wherein the external electrode couples capacitively to the sampled gas.

5. The method of claim 1, wherein the exciting does not require exposing the sampled gas to an internal igniter.

6. The method of claim 2, wherein the external electrode couples inductively to the sampled gas.

7. The method of claim 2, wherein the external electrode couples capacitively to the sampled gas.

8. The method of claim 2, wherein the exciting does not require exposing the sampled gas to an internal igniter.

9. The method of claim 1, wherein detecting utilizes detectors responsive to band widths sufficiently narrow that a plurality of detectors are responsive to a single peak in the emission spectrum.

10. The method of claim 2, wherein detecting utilizes detectors responsive to band widths sufficiently narrow that a plurality of detectors are responsive to a single peak in the emission spectrum.

11. The method of claim 3, wherein detecting utilizes detectors responsive to band widths sufficiently narrow that a plurality of detectors are responsive to a single peak in the emission spectrum.

12. The method of claim 4, wherein detecting utilizes detectors responsive to band widths sufficiently narrow that a plurality of detectors are responsive to a single peak in the emission spectrum.

13. The method of claim 1, wherein detecting in real time utilizes detectors responsive to the emitted radiation in 20 ms. or less.

14. The method of claim 1, wherein the detectors are shallow junction devices.

15. The method of claim 14, wherein the shallow junction devices are CCDs.

16. The method of claim 1, wherein detecting utilizes deep junction devices.

17. The method of claim 1, wherein detecting utilizes an array of 512 or more detectors.

18. The method of claim 1, wherein detecting utilizes an array of 1024 or more detectors.

19. The method of claim 1, wherein detecting utilizes an array of 2048 or more detectors.

20. A method of obtaining data regarding a process in a reaction chamber, comprising:
    sampling gas outside a reaction chamber that has passed through the reaction chamber during a process;
    exciting the sampled gas by inductive or capacitive coupling to emit radiation; and
    detecting in real time from the emitted radiation a plurality of wave bands of an emission spectrum.

21. The method of claim 20, wherein exciting does not require exposing the sampled gas to an internal igniter.

22. The method of claim 20, wherein sampling includes sampling at least one exhaust gas stream.

23. The method of claim 22, wherein at least a portion of the exhaust gas stream diffuses into the excitation chamber, which is offset from the exhaust gas stream flow.

24. The method of claim 22, wherein the exhaust gas stream passes through the excitation chamber.

25. The method of claim 20, wherein detecting utilizes detectors responsive to hand widths sufficiently narrow that a plurality of detectors are responsive to a single peak in the emission spectrum.

26. The method of claim 20, wherein detecting in real time utilizes detectors responsive to the emitted radiation in 20 ms. or less.

27. The method of claim 20, wherein the detectors are hallow junction devices.

28. The method of claim 27, wherein the shallow junction devices are CCDs.

29. The method of claim 20, wherein detecting utilizes deep junction devices.

30. The method of claim 20, wherein detecting utilizes an array of 512 or more detectors.

31. The method of claim 20, wherein detecting utilizes an array of 1024 or more detectors.

32. The method of claim 20, wherein detecting utilizes an array of 2048 or more detectors.

33. A method of obtaining data regarding a process in a reaction chamber, comprising:
sampling gas outside a reaction chamber that has passed through the reaction chamber during a process;
exciting the sampled gas to emit radiation; and
detecting in real time from the emitted radiation a plurality of wave bands of an emission spectrum, utilizing detectors responsive to band widths sufficiently narrow that a plurality of detectors are responsive to a single peak in the emission spectrum.

34. The method of claim 33, wherein the sampling includes at least one exhaust gas stream from the reaction chamber, wherein at least a portion of the exhaust gas stream diffuses into the excitation chamber, which is offset from the exhaust gas stream flow.

35. The method of claim 33, wherein the sampling includes at least one exhaust gas stream from the reaction chamber which passes through the excitation chamber.

36. The method of claim 33, wherein exciting utilizes an external electrode which couples inductively to the sampled gas.

37. The method of claim 33, wherein exciting utilizes an external electrode which couples capacitively to the sampled gas.

38. The method of claim 33, wherein exciting does not require exposing the sampled gas to an internal igniter.

39. The method of claim 33, wherein detecting in real time utilizes detectors responsive to the emitted radiation in 20 ms. or less.

40. The method of claim 33, wherein the detectors are shallow junction devices.

41. The method of claim 40, wherein the shallow junction devices are CCDs.

42. The method of claim 33, wherein detecting utilizes deep junction devices.

43. The method of claim 33, wherein detecting utilizes an array of 512 or more detectors.

44. The method of claim 33, wherein detecting utilizes an array of 1024 or more detectors.

45. The method of claim 33, wherein detecting utilizes an array of 2048 or mow detectors.

46. A method of obtaining data regarding a process in a reaction chamber, comprising:
sampling gas outside a reaction chamber that has passed through the reaction chamber during a process;
exciting the sampled gas with an energy to emit radiation.
detecting in real time from the emitted radiation a plurality of wave bands of an emission spectrum; and
adjusting the energy in real time to increase or decrease the emitted radiation.

47. A method of real time control of a process in a reaction chamber, comprising:
sampling gas outside a reaction chamber that has passed through the reaction chamber during a process;
exciting the sampled gas to emit radiation;
detecting in real time from the emitted radiation a plurality of wave bands of an emission spectrum; and
controlling die process in real time based on the detected wave bands.

48. The method of claim 47, wherein the process includes cleaning the reaction chamber with a plasma comprising fluorine, and wherein the reaction chamber is a deposition chamber.

49. The method of claim 47, wherein the process includes cleaning the reaction chamber with a plasma comprising fluorine, and wherein the reaction chamber is a plasma etching chamber.

50. The method of claim 47, wherein the process includes conditioning a reaction chamber to a predetermined wall condition.

51. The method of claim 47, wherein the process includes calibrating gas flow through the reaction chamber.

52. The method of claim 47, wherein the process produces hydrochlorofluorocarbons.

53. The method of claim 47, wherein controlling the process includes responding to a leak of ambient gas into the reaction chamber.

54. The method of claim 47, wherein controlling the process includes responding to elevated levels of helium.

55. A method of monitoring a process in a reaction chamber comprising:
sampling gas outside a reaction chamber that has passed through the reaction chamber during a process;
exciting the sampled gas to emit radiation;
detecting in real time from the emitted radiation a plurality of wave bands of an emission spectrum; and
displaying to a user in real time a plurality readouts for one or more characteristics of at least a portion of the detected wave bands.

56. The method of claim 47, wherein displaying includes graphing a measure of intensity of at least a portion of the detected wave bands and reporting numeric values for the measure of intensity and the wave length of a user selected point on the graph.

57. The method of claim 47, wherein displaying includes representing a measure of intensity of at least a portion of the detected wave bands by a line graph and by an intensity graph.

58. The method of claim 57, wherein the intensity graph is displayed as a bright line spectrum.

59. The method of claim 57, wherein the intensity graph is displayed as a dark line spectrum.

60. The method of claim 47, wherein displaying includes user selection of a plurality of wave lengths and a strip chart display of the selected wave lengths.

61. The method of claim 47, wherein displaying includes user selection of an algebraic combination of a plurality of wave lengths and a strip chart display of the algebraic combination.

62. The method of claim 47, wherein displaying includes user selection of a derivative function of a wave length and a strip chart display of the wave length and the derivative function.

63. The method of claim 47, wherein displaying includes user selection of parameters for integration time for the detection of the wave bands, number of the integrated detections averaged, and smoothing of the averaged integrated detections.

64. The method of claim 63, wherein the user selection is made graphically.

65. The method of claim 63, wherein the user selection is made numerically.

66. A method of obtaining a quantitative measure of an unknown flow gas having a known spectral peak, comprising:

introducing a known flow of reference gas having a known spectral peak into a reaction chamber;

sampling gas outside a reaction chamber that has passed through the reaction chamber;

exciting the sampled gas to emit radiation;

detecting in real time wave bands, corresponding to the known spectral peaks of the known flow reference gas and the unknown flow gas, from the emitted radiation; and determining a quantitative measure of the unknown flow gas from of the detected wave bands.

67. The method of claim 66, wherein the reference gas it argon.

68. The method of claim 66, wherein the known spectral peak of the reference gas is centered at about 750 nm.

69. The method of claim 66, wherein the determining step includes applying a non-linear fit of spectral ratios for flows of the unknown flow and reference gasses to a ratio of the detected wave bands.

70. The method of claim 66, further including controlling a process in the reaction chamber based on the determined flow of the unknown flow gas.

71. The method of claim 70, wherein controlling the process includes adjusting a mass flow controller.

72. The method of claim 70, wherein controlling the process includes determining the endpoint of the process.

* * * * *

UNITED STATES PATENT AND TRADEMARK OFFICE
CERTIFICATE OF CORRECTION

PATENT NO. : 6,757,061 B2
APPLICATION NO. : 10/321130
DATED : June 29, 2004
INVENTOR(S) : Gary Powell It is certified that error appears in the above-identified patent and that said Letters Patent is hereby corrected as shown below:

Column 10, claims 56-57 and 60-63 should read as follows:

56. The method of claim 55, wherein displaying includes graphing a measure of intensity of at least a portion of the detected wave bands and reporting numeric values for the measure of intensity and the wave length of a user selected point on the graph.

57. The method of claim 55, wherein displaying includes representing a measure of intensity of at least a portion of the detected wave bands by a line graph and by an intensity graph.

60. The method of claim 55, wherein displaying includes user selection of a plurality of wave lengths and a strip chart display of the selected wave lengths.

61. The method of claim 55, wherein displaying includes user selection of an algebraic combination of a plurality of wave lengths and a strip chart display of the algebraic combination.

62. The method of claim 55, wherein displaying includes user selection of a derivative function of a wave length and a strip chart display of the wave length and the derivative function.

63. The method of claim 55, wherein displaying includes user selection of parameters for integration time for the detection of the wave bands, number of the integrated detections averaged, and smoothing of the averaged integrated detections.

Signed and Sealed this

Sixth Day of March, 2007

JON W. DUDAS
*Director of the United States Patent and Trademark Office*